United States Patent [19]

Gasparski et al.

[11] Patent Number: 5,250,676

[45] Date of Patent: Oct. 5, 1993

[54] PROCESS FOR THE PREPARATION OF 3-SUBSTITUTED-2-AZETIDINONES

[75] Inventors: Catherine M. Gasparski, Irvine, Calif.; Marvin J. Miller, South Bend; Min Teng, Mishawaka, both of Ind.

[73] Assignee: University of Notre Dame du Lac, Notre Dame, Ind.

[21] Appl. No.: 855,402

[22] Filed: Mar. 23, 1992

[51] Int. Cl.[5] .............. C07D 205/85; C07D 205/08; C07F 39/00; C07F 45/06
[52] U.S. Cl. ........................... 540/200; 540/205; 540/355; 540/360; 540/362; 540/363; 540/364
[58] Field of Search ............. 540/200, 360, 362, 363, 540/364, 205, 355

[56] References Cited

PUBLICATIONS

Gasparski, JACS 114, 2741 (1992).
Atanu, B., and Miller, M., "Rearrangement of N-(-p-toluenesulfonyloxy)-2-pyrrolidinone," *Heterocycles*, 26, No. 11, 2849 (1987).

*Primary Examiner*—Mark L. Berch
*Attorney, Agent, or Firm*—James J. Sales; Leroy Whitaker

[57] ABSTRACT

Provided is a process for diastereoselectively preparing compounds of the formula

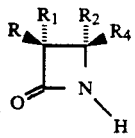

which includes the step of subjecting a compound of the formula

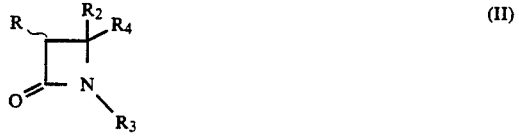

to a salt whose anion is a nucleophilic base whose conjugate acid has a pKa in the range of between about −7 to about 14, or a silylated derivative of the salt; wherein
$R_1$ is said nucleophile;
R is hydrogen, or protected amino,
$R_2$ is $R_4$ as defined herein below;
$R_3$ is a leaving group; and
$R_4$ is hydrogen, $C_1$-$C_6$ alkyl, or a group of the formula

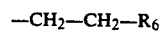

wherein
$R_6$ is 2-furyl, naphthyl, phenyl, phenyl substituted with 1, 2 or 3 substituents selected from $C_1$-$C_6$ alkyl, $C_1$-$C_6$ alkoxy, $C_1$-$C_6$ alkylthio, nitro, halo, carboxy and amido; or
$R_6$ is a group of the formula

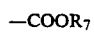

or

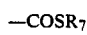

in which
$R_7$ is selected from $C_1$-$C_6$ alkyl, $C_2$-$C_6$ alkenyl, benzyl, phenyl, or benzyl or phenyl substituted with 1, 2 or 3 substituents selected from $C_1$-$C_6$ alkyl, $C_1$-$C_6$ alkoxy, $C_1$-$C_6$ alkylthio, nitro, halo, carboxy and amido; or
$R_4$ is a group of the formula

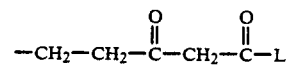

(Abstract continued on next page.)

-continued
or
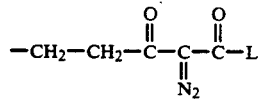
wherein
L is —OR$_7$ where R$_7$ is as defined; or
R$_4$ is a group of the formula
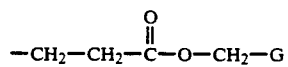
wherein:
G is trimethylsilylmethyl, hydrogen, C$_1$-C$_6$ alkyl, C$_1$-C$_6$ substituted alkyl, phenyl, or phenyl substituted with 1, 2 or 3 substituents selected from C$_1$-C$_6$ alkyl, C$_1$-C$_6$ alkoxy, C$_1$-C$_6$ alkylthio, nitro, halo, carboxy and amido.
6 Claims, No Drawings

PROCESS FOR THE PREPARATION OF 3-SUBSTITUTED-2-AZETIDINONES

DESCRIPTION OF THE INVENTION

This invention relates to β-lactams, and more particularly to a process for preparing 3-substituted-2-azetidinones.

While investigating alternative methods for the synthesis of the carbacephem class of β-lactam antibiotics via azetidinone precursors, a novel reaction for diastereoselective C-3 azide placement and cleavage of the N—O bond on N-hydroxy-β-lactams was discovered. Upon further work, it was determined that various N—OR cleavages with diastereoselective C-3 nucleophilic placement on the azetidinone could be accomplished.

The process of the invention provides compounds of the formula

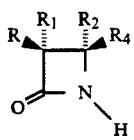
(I)

by subjecting a compound of the formula

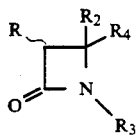
(II)

to a nucleophile the source of which is a base whose conjugate acid has a pKa in the range of between about −7 to 14, or a salt of such base or a silylated derivative of the nucleophile.

In the process, $R_1$ is the nucleophile; R is hydrogen, amino, protected amino, or a group of the formula

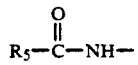

wherein $R_5$ is the residue of a carboxylic acid;
$R_2$ is $R_4$, as hereinbelow defined;
$R_3$ is a leaving group; and
$R_4$ is hydrogen, $C_1$–$C_6$ alkyl, $C_1$–$C_6$ alkyl substituted by halo or —SPh, or
$R_4$ is a group of the formula

—CH$_2$—CH$_2$—R$_6$ or

wherein $R_6$ is 2-furyl, naphthyl, phenyl, phenyl substituted with 1, 2 or 3 substituents selected from $C_1$–$C_6$ alkyl, $C_1$–$C_6$ alkoxy, $C_1$–$C_6$ alkylthio, nitro, halo, carboxy and amido; or $R_6$ is a group of the formula

—COOR$_7$ or

—COSR$_7$ in which $R_7$ is selected from $C_1$–$C_6$ alkyl, $C_2$–$C_6$ alkenyl, benzyl, phenyl, or benzyl or phenyl substituted with 1, 2 or 3 substituents selected from $C_1$–$C_6$ alkyl, $C_1$–$C_6$ alkoxy, $C_1$–$C_6$ alkylthio, nitro, halo, carboxy and amido;
or
$R_4$ is a group of the formula

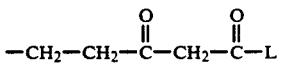

or

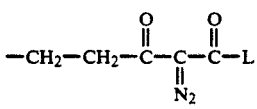

wherein L is —OR$_7$ where $R_7$ is as defined; or
$R_4$ is a group of the formula

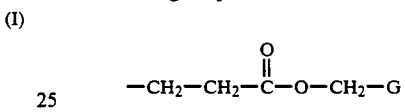

wherein G is trimethylsilylmethyl, hydrogen, $C_1$–$C_6$ alkyl, $C_1$–$C_6$ substituted alkyl, phenyl, or phenyl substituted with 1, 2 or 3 substituents selected from $C_1$–$C_6$ alkyl, $C_1$–$C_6$ alkoxy, $C_1$–$C_6$ alkylthio, nitro, halo, carboxy and amido.

The term "protected amino" refers to an amino having therein a substituent employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxy-carbonyl, 2-(4-toluylsulfonyl)ethoxycarbonyl, 2-(methylsulfonyl)ethoxycarbonyl, 2-(triphenylphosphino)ethoxycarbonyl, 9-fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene and P. G. M. Wuts, "Protective Groups In Organic Synthesis", John Wiley and Sons, New York, N.Y., 1991, Chapter 7.

The term "residue of a carboxylic acid" includes those 7-position side chains known in the cephalosporin and carbocephalosporin arts, and those 6-position side chains known in the penicillin art. Normally, these side chains are residues of $C_1$-$C_{20}$ carboxylic acids. Further examples of such groups may be found in Cook et al., U.S. Pat. No. 4,855,418, incorporated herein by reference.

The term "$C_1$-$C_6$ alkyl" refers to straight and branched chain alkyl groups such as methyl, ethyl, propyl, n-propyl, n-butyl, t-butyl, n-hexyl and like alkyl groups.

The term "$C_1$-$C_6$ substituted alkyl" includes $C_1$-$C_6$ alkyls substituted by halo, $C_1$-$C_6$ alkoxy, cyano, carboxy, trimethylsilyl, amino or $C_1$-$C_6$ alkylthio. Reference is made to U.S. Pat. No. 4,855,418 for further examples of substituted alkyls.

The term "$C_1$-$C_6$ alkoxy" refers to such groups as methoxy, ethoxy, propoxy, t-butyloxy, and like alkoxy groups.

The term "$C_1$-$C_6$ alkylthio" refers to such groups as methylthio, 3-propylthio, t-butylthio, and like alkyl thio groups.

The term "halo" refers to chloro, iodo, bromo, and fluoro.

The term "$C_2$-$C_6$ alkenyl" refers to groups such as ethenyl, 1-propenyl, 2-propenyl, 1-butenyl, 1-pentenyl and like alkenyl groups.

The term "leaving group of the formula —$OR_3'$" designates such groups which under the reaction conditions are cleaved off, or in other words, the N—O bond is cleaved. Illustrative groups for —$OR_3'$ include —O-$SO_nQ$, where n is 1 or 2 and Q is $C_1$-$C_6$ alkyl, $C_1$-$C_6$ substituted alkyl, phenyl or phenyl substituted with 1, 2 or 3 substituents selected from $C_1$-$C_6$ alkyl, $C_1$-$C_6$ alkoxy, $C_1$-$C_6$ alkylthio, nitro, halo, carboxy and amido; or —$OR_3'$ is —OPO(phenyl or substituted phenyl)$_2$; or —$OR_3'$ is —OPO($C_1$-$C_6$ alkyl or substituted alkyl)$_2$; or —$OR_3'$ is —OPO(OQ)$_2$; or —$OR_3'$ is $O_2NO$; or —$OR_3'$ is a group of the formula

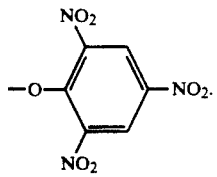

Other acceptable leaving groups may be found in Noyce, D. S. and Vigilio, J. A., *J. Org. Chem.* 1972, 37, 2643, incorporated herein by reference.

Inert aprotic solvents which can be used are aprotic organic solvents, for example, tetrahydrofuran, tetrahydropyran, dioxane, acetonitrile, diethyl ether, dimethylformamide, dimethylacetamide, 1,2-dimethoxyethane, and like solvents. Mixtures of such solvents may be used. Preferred solvents are acetonitrile and dichloromethane.

Preferably, the process is substantially anhydrous, or carried out in the absence of water. While trace amounts of water are tolerable, the minimum should be present.

The souce of the nucleophile may be a base whose conjugate acid has a pKa range from about $-7$ to about 14. Such bases include trimethylsilylazide, trimethylsilyliodide, trimethylsilylbromide, p-carboxybenzene sulfonylazide, 2,4,6-triisopropylbenzenesulfonyl azide, tetrabutyl ammonium iodide,diphenylphosphoylazide, and thiophenol. Such conjugate acids include hydrazoic acid, acetic acid, and hydrochloric acid. The nucleophile source may be the salt of such a base, such as $LiR_1$, $NaR_1$, $KR_1$, $CsR_1$, and ammonium salts, and also silylated derivatives of the nucleophile. Such sources provide the anion or nucleophile which substitutes at the 3-position of the azetidinone. Such nucleophiles ($R_1$) include $N_3$, Cl, Br, I, SPh, $C_1$-$C_6$ carboxylates, $C_1$-$C_6$ alkylthiols, and $C_1$-$C_6$ alcohols. The preferred amount of the nucleophile used in the process is 1–2 moles per mole of substrate.

In a preferred embodiment of the process, a tertiary amine base, said as triethylamine, is included in the process. The tertiary amine base is preferably present in an amount of between 1-25 moles per mole of substrate.

The process may be carried out at temperatures of between about 0° to 40° C. with room temperature, 21°-23° C., being preferred.

The process affords both the placement of the nucleophile at the C-3 position diastereoselectively to yield the trans product and also the reduction of the β-lactam N—O bond. Also, a third transformation is provided where $R_4$ is a group of the formula

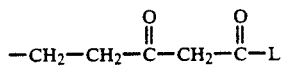

as it is converted to a group of the formula

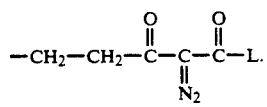

The compounds provided by the process may be further synthesized to provide carbacephalosporins by means known in the art. For example, a 3-azido azetidinone may be reduced to the amine, derivatized and epimerized at the 3-position, and alkylated at the 1-position to form a precursor for Dieckmann cyclization, as described by Jackson et al., *Tetrahedron Letters*, 1990, 31, 6317-6320, incorporated herein by reference. An example of such a compound is

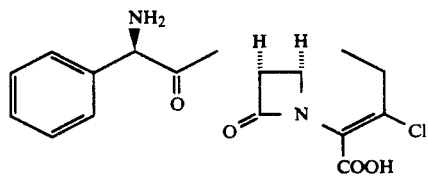

EXPERIMENTAL SECTION

General Methods

NMR spectroscopy utilized a General Electric GN-300 or a Varian VXR 500S spectrometer. Unless stated to the contrary, deuterated chloroform was used as solvent with tetramethylsilane as internal reference for $^1H$ NMR spectra and with the solvent triplet resonance as reference for $^{13}C$ NMR spectra. Infrared data were obtained with a Perkin-Elmer Model 1420 spectrophotometer (referenced to polystyrene) either neat, as films evaporated from solutions with volatile solvents, or as KBr pellets. Mass spectral data were obtained on a Finnagan MAT Model 8430 spectrometer by electron impact (EIMS) at 70 eV or by chemical ionization (CIMS) with isobutane unless stated otherwise.

Normal phase flash chromatography was done using Silica Gel $PF_{254}$ (EM Science). Radial chromatography with a Harrison Research Chromatotron Model 7924 or preparatory TLC was performed with Kieselgel 60 $PF_{254}$ (EM Science). TLC work employed aluminum backed plates of 0.2 mm thickness (silica gel 60 $F_{254}$, MCB Reagents); visualization was done with $KMnO_4$, ethanolic phosphomolybdic acid, iodine, and/or by UV light.

Solvents and reagents were obtained from reputable sources and were purified by standard methods before use as necessary. Procedures requiring moisture free conditions were accomplished with anhydrous, purified reagents in oven- and/or flame-dried glassware and syringes under argon atmosphere.

PREPARATION 1 t-Butyl 5-(1-benzyloxy-2-oxo-4-azetidinyl)-3-oxopentanoate

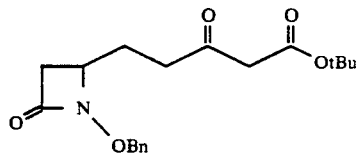

This compound was synthesized according to those procedures outlined in the reference Williams, M. A. and Miller, M. J. *J. Org. Chem.* 1991, 56, 1293.

EXAMPLE 1 t-Butyl 5-(trans 3-azido-2-oxo-4-azetidinyl)-2-diazo-3-oxopentanoate (B) and t-Butyl 5-(trans 3-azido-2-oxo-4-azetidinyl)-3-oxooentanoate (C)

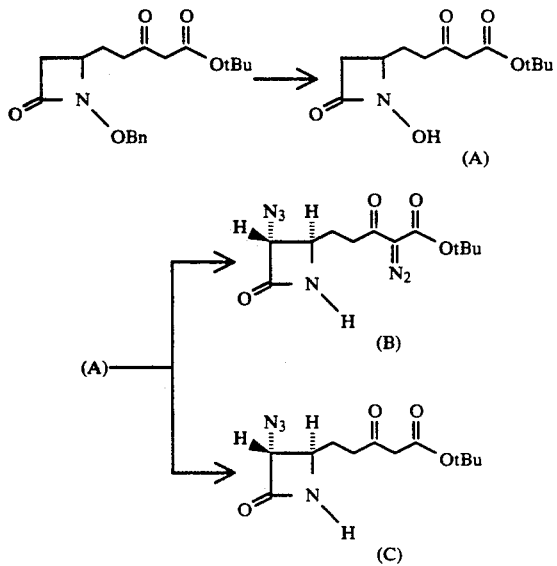

t-Butyl 5-(1-benzyloxy-2-oxo-4-azetidinyl)-3-oxopentanoate (90 mg, 0.26 mmol) was hydrogenated with 10% Pd/C in EtOAc for 1.5 h to yield t-butyl 5-(1-hydroxy-2-oxo-4-azetidinyl)-3-oxopentanoate (A). Compound A was directly taken on to the next step without undue delay. In an ice bath under argon atmosphere, compound A was dissolved in 1 mL of anhydrous $CH_3CN$. The p-carboxybenzenesulfonyl azide (68.0 mg, 0.30 mmol, 110 mol %) was added as a solid followed by 1 mL of solvent as a wash and $Et_3N$ (125 microliter, 91 mg, 0.90 mmol, 330 mol %). The reaction was stirred at ice bath temperature and was gradually allowed to warm to ambient temperature over 1-2 h, and was stirred for a total of 27 h. The reaction eventually turned light brown and a white precipitate formed. The reaction mixture was diluted with 15 mL of $CH_2Cl_2$ and 35 mL of ether, and the solvent was evaporated after filtration to remove the solid. The resulting brown oil was passed through a short plug of silica as a solution in $CH_2Cl_2$ to yield 50 mg of a light brown oil after solvent removal. The oil was chromatographed by column (EtOAc and hexanes as eluting solvents) to yield two fractions as oils: compound B (13 mg, 16% overall yield) and compound C (13 mg, 17% overall yield). The diazo/azido/reduced product B was recrystallized in ether/hexanes to give orange-yellow needles on which X-ray crystallographic data were obtained.

This reaction was repeated on a 0.416 mmol scale to give a mixture of the same two products B and C in crude form.

t-Butyl 5-(trans 3-azido-2-oxo-4-azetidinyl)-2-diazo-3-oxopentanoate (B). $R_f=0.38$ (1:1 EtOAc/hexanes); mp=89.5°-91.0° C. (obtained on white cluster-like crystals recrystallized from minimal volume of ether); $^1H$ NMR δ 6.3 (bs, heteroatom H), 4.286 (apparent t, J=1.8 Hz, 1 H, H-3 azetidinyl), 3.560 (dt, J=2.1, ~6.5 Hz, 1 H, H-4 azetidinyl), 3.018 (dt, J=7.2, 16.8 Hz, 1 H, H-4 pentanoate), 2.862 (dt, J=6.9, 16.8 Hz, 1 H, H-4 pentanoate), 2.147-1.922 (m, 2 H, H-5 pentanoate), 1.532 (s, 9 H), with minor impurities at 1.7 (0.3 H, perhaps contaminating moisture); $^{13}C$ NMR δ 191.65, 163.92, 160.39, 83.68, 69.64, 56.33, 36.10, 28.27, 27.94 (note that the diazo C was not observed); IR (neat as oil) 3100-3400, 2140, 2110, 1780, 1715, 1650 $cm^{-1}$; MS (FAB) gave M+1 at 309.

t-Butyl 5-(trans 3-azido-2-oxo-4-azetidinyl)-3-oxopentanoate (C). $R_f=0.22$ (1:1 EtOAc/hexanes); $^1H$ NMR δ 6.33 (bs, heteroatom H), 4.224 (apparent t, J= ~1.6 Hz, 1 H, H-3 azetidinyl), 3.554 (dt, J=2.1, 6.6 Hz, 1 H, H-4 azetidinyl), 3.386 (apparent d, J=0.9 Hz, 2 H, H-2 pentanoate), 2.784-2.588 (m, 2 H, H-4 pentanoate), 2.11-1.893 (m, 2 H, H-5 pentanoate), 1.47 (s, 10 of the expected 9 H), (small singlet at δ 1.532 (0.7 H) and δ 1.492 (0.7 H) could be due to moisture and enol form of β-keto ester); $^{13}C$ NMR δ 201.94, 166.53, 163.92, 82.64, 69.70, 56.04, 50.27, 38.92, 28.27, 27.96, 26.88 (note the presence of an additional peak upfield which could be due to t-butyl C of enol form of β-keto ester); IR (neat) 3400-3150, 2120, 1780, 1740, 1715 $cm^{-1}$; CIMS on aged sample gave M+1 at 283 and additional peaks due to decomposition (such as M+1 at 508 which could be a dimer of parent ion after $N_2$ loss).

EXAMPLE 2 t-Butyl 5-(trans 3-azido-2-oxo-4-azetidinyl)-2-diazo-3-oxooentanoate (B)

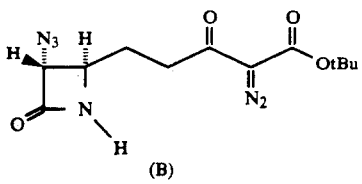

After hydrogenation of r-butyl 5-(1-benzyloxy-2-oxo-4-azetidinyl)-3-oxopentanoate (0.144–0.864 mmol; 50.0–300.2 mg) to obtain compound A, compound A was dissolved in anhydrous $CH_3CN$ (~0.17 mmol/mL) under argon atmosphere and cooled in an ice bath. The p-carboxybenzenesulfonyl azide (330 mol %) was added as a solid followed by $Et_3N$ (550 mol %), and the reaction was allowed to warm to ambient temperature over 1–2 h. The reaction was stirred overnight (~20 h) while protected from direct light. After this time, a white precipitate had formed and the solution was red. Workup was accomplished by diluting the reaction mixture with EtOAc/5% HOAc (1:1, about 10× the original reaction volume). The organic layer was separated and washed with fresh 5% HOAc, brine, saturated $NaHCO_3$ (2×), and brine. After drying over $MgSO_4$, filtering, and removing solvent, the crude product was obtained as a red oil which displayed contaminating p-substituted aromatic signals in the $^1H$ NMR. A second wash of the oil dissolved in EtOAc with saturated $NaHCO_3$ followed by brine and the usual drying procedure eliminated these resonances from the $^1H$ NMR. Passing a concentrated solution of the red oil through a small plug of silica removed a highly colored polar side product to yield a light yellow oil. Crude yields have ranged 34–60%. Note that changing the workup procedure to include a 20 h stirring step with 1000–2000 mol % HOAc gave crude yield on the higher side of this range (60%). For additional purification, column chromatography (80:20 hexanes/EtOAc) could be employed followed by trituration with ether. After recrystallization in ether, the product was obtained as white, cluster-like crystals in 27% yield.

EXAMPLE 3 t-Butyl 5-(1-benzyloxy-2-oxo-4-azetidinyl)-2-diazo-3-oxopentanoate

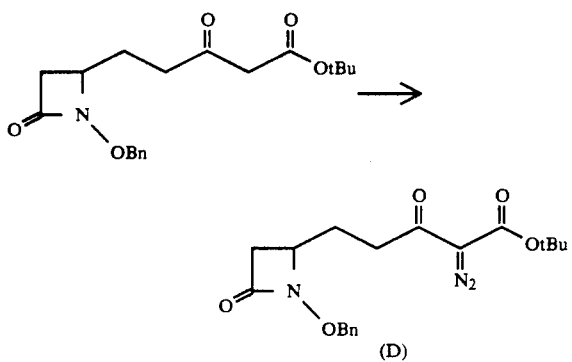

t-Butyl 5-(1-benzyloxy-2-oxo-4-azetidinyl)-3-oxopentanoate (20 mg, 0.058 mmol) was reacted under the same optimized conditions as above with p-carboxybenzenesulfonyl azide (43 mg, 0.19 mmol, 330 mol %) and $Et_3N$ (44 microliters, 0.317 mmol, 550 mol %) to yield, after aqueous workup, 19.8 mg of a colorless oil. This product was determined to be t-butyl 5-(1-benzyloxy-2-oxo-4-azetidinyl)-2-diazo-3-oxopentanoate D by comparison of TLC, IR, and $^1H$ NMR spectra with those from authentic material. The product was about 90% pure as determined by $^1H$ NMR, with p-carboxybenzene azide or p-carboxybenzene sulfonamide as probable contaminants. Taking these impurities into account, an estimated crude yield was 86%.

EXAMPLE 4 t-Butyl 5-(2-oxo-4-azetidinyl)-3-oxopentanoate (E)

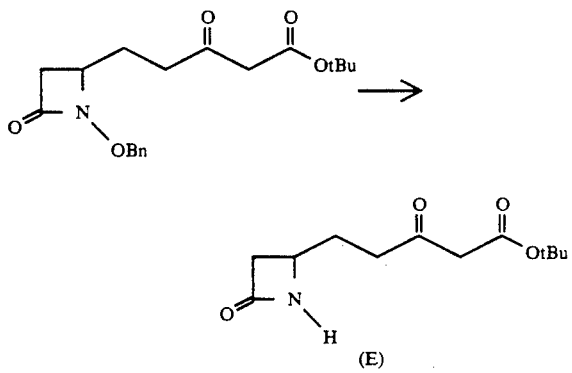

t-Butyl 5-(1-benzyloxy-2-oxo-4-azetidinyl)-3-oxopentanoate (80 mg, 0.230 mmol) was hydrogenated in EtOAc (~10 mL) in the presence of 10% Pd/C (10% w/w 8.0 mg) for 2 h. The reaction was filtered through Celite and the solvent removed to yield an oil which was immediately used in the next step. The oil was dissolved in 1 mL of anhydrous THF and deoxygenated by bubbling with argon, and the reaction was done under an argon atmosphere. Sodium acetate buffer (4.1M, pH 5.0, 1.6 mL, 6.5 mmol, 2840 mol %), deoxygenated in the same manner, was added via syringe followed immediately by $TiCl_3$ (594 microliters, 0.653 mmol, 284 mol %; 1.1M as determined by titration with $Ce(SO_4)_2$; $TiCl_3$ was obtained from Fluka as an aqueous solution in 20% HCl) which was added slowly via syringe with the needle tip below the surface of the reaction solution. The dark purple reaction was stirred for 2 h and was then quenched by diluting into about 25 mL of 1:1 EtOAc/sodium L-tartrate buffer (0.78M, pH 5.0). The organic layer was separated and was washed with additional tartrate buffer, brine, saturated $Na_2CO_3$ (aq), and brine sequentially. After drying over $MgSO_4$, filtering, and removing solvent, 32.4 mg of a yellow oil was obtained which was determined to be the desired product (58% crude yield) by comparison of $^1H$ NMR and CIMS data with that from authentic material.

EXAMPLE 5 t-Butyl 5-(2-oxo-4-azetidinyl)-2-diazo-3-oxooentanoate

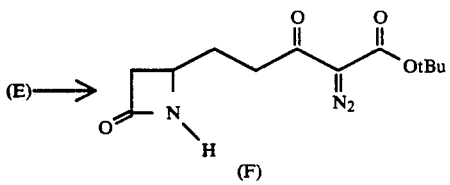

t-Butyl 5-(2-oxo 4-azetidinyl)-3-oxopentanoate E (32.4 mg, 0.134 mmol) was reacted with p-carboxybenzenesulfonyl azide (100 mg, 0.442 mmol, 330 mol %) and Et₃N (102 microliters, 0.737 mmol, 550 mol %) according to the optimized conditions above to yield 42 mg of a yellow oil after aqueous workup. This product was determined to be t-butyl 5-(2-oxo-4-azetidinyl)-2-diazo-3-oxopentanoate F by comparison of $^1$H NMR, IR spectral data with that from authentic material. The product was about 80% pure as determined by $^1$H NMR, with p-carboxybenzene azide or p-carboxybenzene sulfonamide as probable contaminants. Taking these impurities into account, an estimated crude yield was 98%.

PREPARATION 2

2-(Trimethylsilyl)ethyl 3-(1-hydroxy-2-oxo-4 azetidinyl)propionate (H)

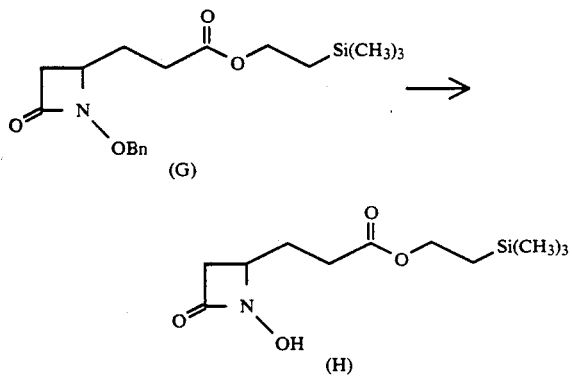

2-(Trimethylsilyl)ethyl 3-(1-benzyloxy-2-oxo-4-azetidinyl)propionate G (62 mg, 0.169 mmol) was deprotected by hydrogenation in the presence of 10% Pd/C (6.5 mg, 10% w/w)in EtOAc according to precedent to yield desired 48 mg of product H as an oil (100% yield). This oil was immediately used in the next reaction.

EXAMPLE 6

2(Trimethylsilyl)ethyl 3-(trans 3-azido-3-oxo-4-azetidinyl)-propionate (I)

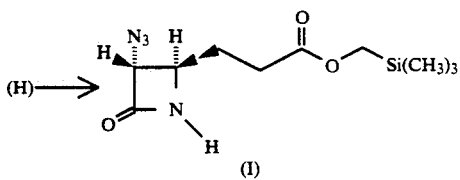

2-(Trimethylsilyl)ethyl 3-(1-hydroxy-2-oxo-4-azetidinyl)propionate H (48 mg, 0.17 mmol) was reacted with p-carboxybenzenesulfonyl azide (127 mg, 0.558 mmol, 330 mol %) and Et₃N (129 microliters, 0.930 mmol, 550 mol %) according to the conditions above to yield 52 mg of a reddish brown oil after aqueous workup. This product was chromatographed by column (1:1 EtOAc/hexanes) to yield 15 mg of a colorless oil (31% yield), I. R$_f$=0.42 (1:1 EtOAc/hexanes); $^1$H NMR δ 6.25 (bs, heteroatom H), 4.25 (apparent t, J=1.5 Hz, 1 H, H-3 azetidinyl), 4.183 (m, 2 H, H-1 ester), 3.568 (dt, J=~2.2, 6.5 Hz, 1 H, H-4 azetidinyl), 2.400 (t, J=7.0 Hz, 2 H, H-2 propionate), 2.005 (m, 2 H, H-3 propionate), 0.983 (m, 2 H, H-2 ester), 0.042 (m, 9 H, Si(CH₃)₃); $^{13}$C NMR δ 172.38, 163.97, 69.62, 63.26, 56.32, 30.82, 28.42, 17.33, −1.56; IR (neat) 3200–3400, 2950, 2900, 2100, 1780, 1730 cm$^{-1}$; HRMS (EI) calcd. for C₁₁H₂₀N₄O₃Si (M-42,) 256.1243, found 256.1244.

EXAMPLE 7 t-butyl 5-(trans 3-azido-2-oxo-4-azetidinyl)-2-diazo-3-oxooentanoate (B)

(A)  (B)

Starting material A (42 mg, 0.163 mmol) was reacted under the optimized conditions outlined above to yield B with 2,4,6-triisopropylbenzenesulfonyl azide (177 mg, 0.571 mmol, 350 mol %) in the presence of Et₃N (53 microliters, 0.381 mmol, 233 mol %). Aqueous workup was done in the same manner except no saturated NaHCO₃ was used as a wash. Instead, the crude product was semipurified by column chromatography (1:1 EtOAc/hexanes) to yield 16.2 mg of product contaminated with ≦10% arylsulfonamide byproduct or unreacted arylsulfonyl azide as determined by $^1$H NMR. Crude yield of semipurified product was 30%.

EXAMPLE 8 t-Butyl 3-p-toluenesulfonyloxy-7-azido-8-oxo-1-azabicyclo[4.2.0]oct-2-ene-2-carboxylate. trans isomer (J)

(B)—> 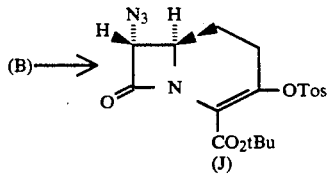

t-Butyl 5-(trans 3-azido-2-oxo-4-azetidinyl)-2-diazo-3-oxopentanoate B (35.7 mg, 0.116 mmol) in crystalline form was dissolved in 2.0 mL of thiophene-free anhydrous benzene. After degassing the solution by bubbling argon through, rhodium acetate (2.6 mg, 5.8 mmol, 5 mol %) was added and the reaction was heated to reflux under argon (external oil bath temperature 91°–95° C.). After 10 min, the starting material was consumed as determined by TLC, and a new less polar spot was present (R$_f$=0.4, 1:1 EtOAc/hexanes). Note that diazo insertion can also be effected with Rh₂(OOct)₄, but purification of J was complicated by their similarities of R$_f$. Since this new compound seemed to be unstable, the reaction mixture was cooled in an ice bath while still under argon atmosphere. After the addition of anhydrous CH$_2$Cl$_2$ (2.0 mL), Et$_3$N (21 microliters, 0.151 mmol, 130 mol %) was added to the solution followed immediately by p-toluenesulfonic anhydride (45.4 mg, 0.139 mmol, 120 mol %, recrystallized from anhydrous CH$_2$Cl$_2$). The reaction was stirred at ice bath temperature for 45 min and was quenched by diluting with 1:1 EtOAc/5% HOAc (total ~20 mL). The organic layer was washed with fresh 5% HOAc, brine, saturated NaHCO$_3$, and again with brine. After drying over MgSO$_4$ and filtering, the solvent was evaporated to leave ~40 mg of a yellow oil which contained unreacted p-toluenesulfonic anhydride. Carbacephalosporin J was most effectively purified by preparatory chromatography on two 20×20 cm aluminum-backed TLC plates of 0.2 mm thickness (developed 75% of the way up thrice with 80:20 hexanes/EtOAc as solvent system). A colorless oil, 20.5 mg, was obtained which crystallized upon storage at 4° C. (41% yield). The solid was recrystallized with EtOAc/hexanes to yield 12.3 mg of cotton-like crystals (24% yield). R$_f$=0.09 (80:20 hexanes/EtOAc); mp=98.5°-101.5° C.; $^1$H NMR δ 7.850 (d, J=8.0 Hz, 2 H, aromatic H), 7.365 (d, J=8.0 Hz, 2 H, aromatic H), 4.240 (d, J=2.0 Hz, 1 H, H-7), 3.588 (ddd, J=2.0, 3.5, 12.0 Hz, 1 H, H-6), 2.510 (m, 2 H, H-2), 2.463 (s, 3 H, CH$_3$), 2.31-2.26 (m, 1 H, H-1), 1.7-1.5 (m, 3 H, H-1 and contaminating HOD), 1.504 (s, 10 of the expected 9 H); $^{13}$C NMR (in CCl$_4$ with deuterated DMSO for signal lock) d 159.7, 156.8, 144.5, 139.3, 132.3, 129.1, 127.2, 121.9, 81.5, 67.7, 53.3, 26.7, 25.2, 22.4, 20.6; IR (KBr pellet) 3600-3300, 3100-2850, 2115, 1775, 1730 cm$^{-1}$; HRMS (EIMS) calcd for C$_{19}$H$_{22}$N$_4$O$_6$S 434.1260, found 434.1254.

PREPARATION 3

2-(Trimethylsilyl)ethyl 3-(1-(Methylbenzenesulfonyloxy)-2-oxo-4-azetidinyl)-propionate (K)

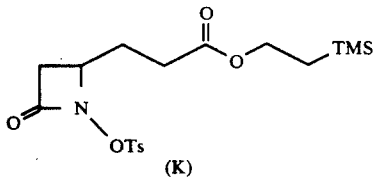

N-Hydroxy-β-lactam which was obtained through hydrogenation of the corresponding N-benzyloxy-β-lactam according to the known procedure was treated with tosyl chloride in the presence of triethylamine in CH$_2$Cl$_2$ (2mL). After stirring in ice bath for one hour, the reaction mixture was concentrated in vacuo followed by column chromatography to yield K in 90%. $^1$H NMR δ 0.059 (s, 9H), 0.98-1.03 (m, 2H), 1.94-2.05 (m, 1H), 2.22-2.29 (m, 1H), 2.40-2.51 (m, 3H), 2.48 (s, 3H), 2.85-2.92 (dd, J$_1$=5.99, J$_2$=14.37, 1H), 4.08-4.11 (m, 1H), 4.16-4.22 (m, 2H), 7.38-7.40 (d, J=8.08, 2H), 7.88-7.90 (d, J=8.39, 2H); IR (neat film) 2955, 1800, 1760, 1595, 1180, 1250, 1180 cm$^{-1}$.

EXAMPLE 9

2-(Trimethylsilyl)ethyl 3-(trans 3-azido-2-oxo-4-azetidinyl)-propionate (L)

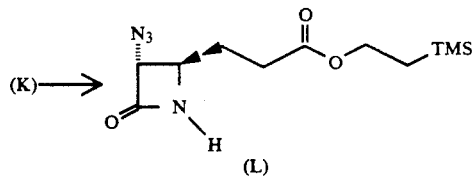

N-Benzenesulfonyloxy-β-lactam K was dissolved in acetonitrile. To the above solution was added trimethylsilyl azide and triethylamine. This reaction mixture was left at room temperature for 12 hours followed by concentration and column chromatography to afford L as colorless oil (62%). $^1$H NMR δ 6.25 (bs, heteroatom H), 4.25 (apparent t, J=1.5 Hz, 1 H, H-3 azetidinyl), 4.183 (m, 2H, H-1 ester), 3.568 (dt, J=~2.2, 6.5 Hz, 1 H, H-4 azetidinyl), 2.400 (t, J=7.0 Hz, 2 H, H-2 propionate), 2.005 (m, 2 H, H-3 propionate), 0.983 (m, 2 H, H-2 ester), 0.042 (m, 9 H, Si(CH$_3$)$_3$); $^{13}$C NMR δ 172.38, 163.97, 69.62, 63.26, 56.32, 30.82, 28.42, 17.33,-1.56; IR (neat) 3200-3400, 2950, 2900, 2100. 1780, 1730 cm$^{-1}$; HRMS (EI) calcd. for C$_{11}$H$_{20}$N$_4$O$_3$Si (M-42,) 256.1243, found 256.1244.

EXAMPLE 10

3(R)-Azido-4(R)-methyl-2-oxo-4-azetidine (N)

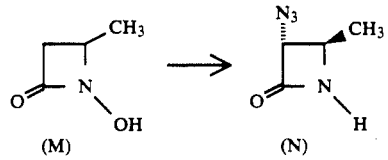

N-Hydroxyl-4(R)-methyl-2-oxo-4-azetidine M (26 mg 0.26 mmol) was treated with triethylamine (0.085 mL, 0.61 mmol) and diphenyl phosphoyl azide (0.07 mL, 0.29 mmol) in acetonitrile. The reaction mixture was left for over night and purified by column chromatography (1:2 EtOAc/hexanes) to yield N as colorless oil (18 mg, 56%). $^1$H NMR δ 1.42-1.44 (d, J=6.2, 3H), 3.65-3.72 (dq, J$_1$=2.04, J$_2$=6.21, 1H), 4.14-4.16 (t, J=1.75, 1H), 6.50 (b, 1H); $^{13}$C NMR δ 19.24, 52.75, 70.80, 164.11; IR (neat) 3265, 2975, 2110, 1760, 1260 cm$^{-1}$.

EXAMPLE 11

2-(Trimethylsilyl)ethyl 3-(trans-3-iodo-2-oxo-4-azetidinyl)-propionate (O)

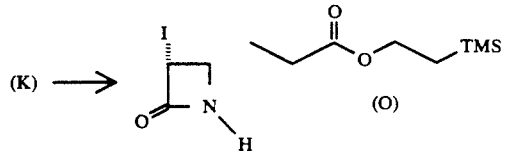

N-Tosyloxy-β-lactam K (25 mg) was treated with tetrabutylammonium iodide and triethylamine in acetonitrile at room temperature for 12 hours. After concentration, the residue was purified by column chromatography (1:2 EtOAc/hexanes) to afford O as colorless oil (12 mg, 54%). $^1$H NMR δ 0.052 (s, 9H), 0.97–1.03 (m, 2H), 2.00–2.05 (m, 2H), 2.39–2.44 (m, 2H), 3.85–3.90 (dt, $J_1=2.00$, $J_2=6.53$, 1H), 4.16–4.22 (m, 2H), 4.55–4.57 (t, $J=2.12$, 1H), 6.12 (b, 1H); IR (neat) 3270, 2950, 1760, 1725, 1250, 1170, 1055; Elemental Anal. for $C_{11}H_{20}INO_3Si$, calcd: C, 35.8; H, 5.40; N, 3.79, Found: C, 36.00; H, 5.50; N, 3.89.

PREPARATION 4

N-Tosyloxy-4-methylbromo-2-oxo-4-azetidine (P)

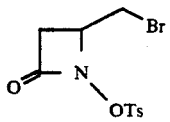

According to the same procedure as for the synthesis of K, the titled compound was obtained (96%). $^1$H NMR δ 2.47 (s, 3H), 2.73–2.79 (dd, $J_1=3.24$, $J_2=14.68$, 1H), 2.93–3.00 (dd, $J_1=6.06$, $J_2=14.70$, 1H), 3.60–3.66 (dd, $J_1=6.73$, $J_2=11.26$, 1H), 3.74–3.79 (dd, $J_1=3.11$, $J_2=11.19$, 1H), 4.25–4.30 (m, 1H), 7.38–7.40 (d, $J=8.13$, 2H), 7.90–7.92 (d, $J=8.84$, 2H); IR (neat) 3065, 2975, 1805, 1730, 1380, 1190, 1025 cm$^{-1}$.

EXAMPLE 12

3-Bromo-4-methylbromo-2-oxo-4-azetidine (O);
3-Thiophenyl-4-methylbromo-2-oxo-4-azetidine (R);
3-Bromo-4-methylthiophenyl-2-oxo-4-azetidine (S)

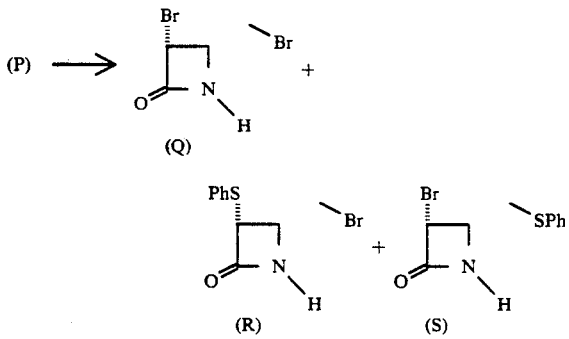

N-Tosyloxy-4-methylbromo-2-oxo-4-azetidine P (285 mg, 0.85 mmol) was treated with thiophenol (0.088 mL, 0.86 mmol) and triethylamine (0.12 mL, 0.86 mmol) in acetonitrile (2 mL). This reaction mixture was left for 12 hours when it became dark brown. After concentration, the residue was purified by column chromatography (1:2 EtOAc/hexanes) to furnish Q, R, and S in a ratio of 2:1:1 (18%).

Q: $^1$H NMR δ 3.49–3.55 (dd, $J_1=7.04$, $J_2=10.87$, 1H), 3.59–3.65 (dd, $J_1=5.21$, $J_2=10.76$, 1H), 4.07–4.12 (m, 1H), 4.56–4.57 (t, $J=1.75$, 1H);

R: $^1$H NMR δ 3.44–3.50 (dd, $J_1=7.97$, $J_2=10.62$, 1H), 3.60–3.65 (dd, $J_2=4.27$, $J_2=10.62$, 1H), 3.74–3.78 (m, 1H), 4.08 (s, 1H), 5.96 (b, 1H), 7.31–7.59 (m, 5H); IR (neat) 3250, 1765, 1475, 1435, 740 cm$^{-1}$;

S: $^1$H NMR δ 3.05–3.12 (dd, $J_1=7.6$, $J_2=13.68$, 1H), 3.20–3.27 (dd, $J_1=6.22$, $J_2=13.96$, 1H), 3.89–3.94 (m, 1H), 4.47–4 48 (t, $J=1.79$, 1H), 6.50 (b, 1H), 7.32–7.47 (m, 5H).

PREPARATION 5

N-Tosyloxy-4(R)-methyl-2-oxo-4-azetidine (T)

According to the same procedure as for the synthesis of compound K, the titled compound was obtained (77%). mp: 86°–88° C.; $^1$H NMR δ 1.41–1.43 (d, $J=6.12$, 3H), 2.37–2.43 (dd, $J_1=3.05$, $J_2=14.27$, 1H), 2.47, (s, 3H), 2.91–30 2.96 (dd, $J_1=6.51$, $J_2=14.28$, 1H), 4.06–4.11 (m, 1H), 7.37–7.40 (d, $J=8.42$, 2H), 7.87–7.90 (d, $J=8.14$, 2H); IR (KBr) 1805, 1380, 1195, 1185, 760 cm$^{-1}$; $^{13}$C NMR δ 17.30, 21.41, 39.50, 55.33, 128.75, 129.71, 130.25, 146.14, 165.43; Ms (CI) 256 (MH+), 214, 155, 102. Elemental Anal. calcd. for $C_{11}H_{13}NO_4S$: C, 51.75; H, 5.13; N, 5.49, Found: C, 51.94; H, 5.33; N, 5.54.

EXAMPLE 13

3(R)-Thiophenyl-4(R)-methyl-2-oxo-4-azetidine (U)

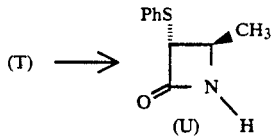

Azetidine T was treated with thiophenol and triethylamine in acetonitrile for 12 hours. This reaction mixture was concentrated in vacuo and purified by column chromatography (1:2 EtOAc/hexanes) to furnish titled compound as colorless oil (18 mg, 22%). mp 65°–67°°C.; 1H NMR δ 1.41–1.43 (d, 6.12, 3H), 3.59–3.65 (dq, $J_1=2.28$, $J_2=6.14$, 1H), 3.92–3.93 (dd, $J_1=1.34$, $J_2=2.13$, 1H), 7.30–7.54 (m, 5H); IR (neat) 3260, 2965, 1755, 1580, 1480, 1435, 1375, 1345 cm$^{-1}$. $^{13}$C NMR δ 166.3, 132.5, 132.4, 129.1, 127.9, 59.4, 52.7, 19.9; Ms (e/m) 193 (M+), 150, 135, 121, 105. HRMS calcd. for $C_{10}H_{11}NOS$: 193.0561, found: 193.0554.

EXAMPLE 14a

O-Tosyl-N-hydroxy-3-phthalimido-2-oxoazetidinone

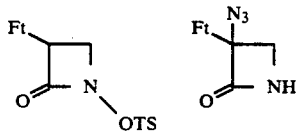

N-Hydroxy-3-phthalimido-2-oxoazetidinone (66 mg, 0.28 mmol) was dissolved in acetonitrile (1 mL). To the above solution was added tosyl chloride (54.2 mg, 0.28 mmol) followed by triethylamine (0.04 mL, 0.28 mmol). The reaction mixture was stirred at room temperature for 2 hours. The white precipitate was filtered out and the clear solution was concentrated under vacuum. The product was purified by column chromatography (E/H, 1:2) to afford colorless crystals (101 mg, 92%).

$^1$H NMR δ 2.48 (s, 3H), 4.09–4.12 (dd, $J_1=5.02$, $J_2=6.03$, 1H), 4.18–4.21(dd, $J_1=3.24$, $J_2=4.95$, 1H), 5.33–5.36 (dd, $J_1=3.24$, $J_2=6.09$, 1H), 7.44–7.46 (d, $J=8.02$ 2H), 7.78–7.91 (m, 4H), 8.05–8.08 (d, $J=8.42$, 2H); $^{13}$C NMR δ 21.9, 50.6, 52.1, 123.9, 129.5, 120.1, 130.4, 131.5, 134.7, 146.7, 161.3, 166.4; IR (KBr) 2980, 1795, 1720, 1400, 1200, 715 cm$^{-1}$; Ms m/e 214, 186, 172, 132, 104, 91, 76.

EXAMPLE 14b

3-Azido-3-phthalimido-2-oxoazetidinone

To a solution of O-tosyl-N-hydroxy-3-phthalimido-2-oxoazetidinone (45 mg, 0.12 mmol) in acetonitrile (1 mL) was added TMSN$_3$ (0.023 mL) followed by triethylamine (0.02 mL, 0.14 mmol). The reaction mixture was left at room temperature for 17 hours. The solution was evaporated to dryness and the residue was purified by column chromatography (E/H, 1:1) to yield desired product as white crystals (18 mg, 60%).

$^1$H NMR δ 3.77–3.79 (d, J=6.9, 1H), 4.09–4.11 (d, J=6.87, 1H), 6.19 (b, 1H), 7.80–7.82 (m, 2H), 7.92–7.94 (m, 2H); IR (KBr) 3325, 2220, 1805, 1755, 1720, 1460, 1355, 1335, 1235, 1150, 720 cm$^{-1}$; Ms m/e 229 (M$^+$-28), 214, 186, 167, 149, 132, 104 (base peak); HRMS calcd for C$_{11}$H$_7$N$_3$O$_3$ (M$^+$-28) 229.04874, found 229.0489. stop

We claim:

1. A process for the preparation of compounds of the formula

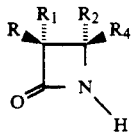
(I)

which comprises the step of subjecting a compound of the formula

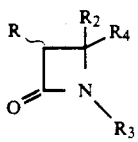
(II)

to a salt whose anion is a nucleophilic base whose conjugate acid has a pKa in the range of between about −7 to about 14; wherein R$_1$ is said nucleophile;
R is hydrogen,
R$_2$ is hydrogen or C$_1$–C$_6$ alkyl;
R$_3$ is a leaving group selected from —OSO$_n$O, where n is 1 or 2 and O is C$_1$–C$_6$ alkyl, C$_1$–C$_6$ substituted alkyl, phenyl or phenyl substituted with 1, 2, or 3 substituents selected from C$_1$–C$_6$ alkyl, C$_1$–C$_6$ alkoxy, C$_1$–C$_6$ alkylthio, nitro, halo, carboxy and amido; OPO(phenyl or substituted phenyl)$_2$; —O-PO(C$_1$–C$_6$ alkyl or substituted alkyl)$_2$; —OPO(OO)$_2$; O$_2$NO; or a group of the formula

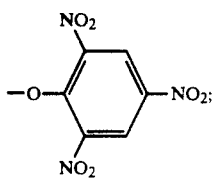

and
R$_4$ is hydrogen, C$_1$–C$_6$ alkyl, or a group of the formula

—CH$_2$CH$_2$—R$_6$ wherein
R$_6$ is 2-furyl, naphthyl, phenyl, phenyl substituted with 1, 2 or 3 substituents selected from C$_1$–C$_6$ alkyl, C$_1$–C$_6$ alkoxy, c$_1$–C$_6$ alkylthio, nitro, halo, carboxy and amido; or
R$_6$ is a group of the formula

—COOR$_7$ or

—COSR$_7$ in which
R$_7$ is selected from C$_1$–C$_6$ alkyl, C$_2$–C$_6$ alkenyl, benzyl, phenyl, or benzyl or phenyl substituted with 1, 2 or 3 substituents selected from C$_1$–C$_6$ alkyl, C$_1$–C$_6$ alkoxy, C$_1$–C$_6$ alkylthio, nitro, halo, carboxy and amido; or
R$_4$ is a group of the formula

or

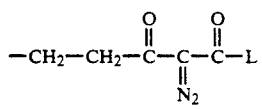

wherein
L is —OR$_7$ where R$_7$ is as defined; or
R$_4$ is a group of the formula

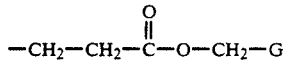

wherein:
G is trimethylsilylmethyl, hydrogen, C$_1$–C$_6$ alkyl, C$_1$–C$_6$ substituted alkyl, phenyl, or phenyl substituted with 1, 2 or 3 substituents selected from C$_1$–C$_6$ alkyl, C$_1$–C$_6$ alkoxy, C$_1$–C$_6$ alkylthio, nitro, halo, carboxy and amido.

2. The process as recited in claim 1 wherein said nucleophile is selected from N$_3$, Cl, Br, I, SPh, C$_1$–C$_6$ carboxylates, C$_1$–C$_6$ alkylthiols, or C$_1$–C$_6$ alcohols.

3. The process as recited in claim 1 wherein the step is conducted at a temperature of between about 0°–40° C.

4. The process as recited in claim 1 wherein R$_1$ is azide or iodo, R$_3$ is methylbenzenesulfonyloxy, and R$_4$ is a group of the formula

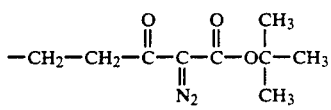

5. The process as recited in claim 4 further comprising the step of cyclizing the compound of formula (I) to produce

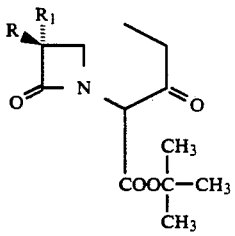
(III)

6. A process for the preparation of compounds of the formula

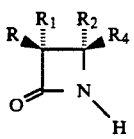
(I)

which comprises the step of subjecting a compound of the formula

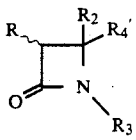
(III)

to the nucleophile $R_1$ which is azide; wherein
R is hydrogen,
$R_2$ is hydrogen or $C_1$-$C_6$ alkyl;
$R_3$ is a leaving group selected from —$OSO_nO$, where n is 1 or 2 and O is $C_1$-$C_6$ alkyl, $C_1$-$C_6$ substituted alkyl, phenyl or phenyl substituted with 1, 2, or 3 substituents selected from $C_1$-$C_6$ alkyl, $C_1$-$C_6$ alkoxy, $C_1$-$C_6$ alkylthio, nitro, halo, carboxy and amido; OPO(phenyl or substituted phenyl)$_2$; —O-PO($C_1$-$C_6$ alkyl or substituted alkyl)$_2$; —OPO(OO)$_2$; $O_2NO$; or a group of the formula

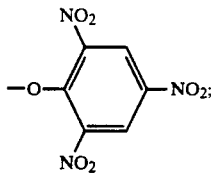

$R_4'$ is a group of the formula

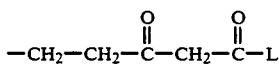

and
$R_4$ is a group of the formula

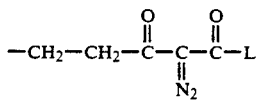

wherein
L is —$OR_7$ where $R_7$ is selected from $C_1$-$C_6$ alkyl, $C_2$-$C_6$ alkenyl, benzyl, phenyl, or benzyl or phenyl substituted with 1, 2 or 3 substituents selected from $C_1$-$C_6$ alkyl, $C_1$-$C_6$ alkoxy, $C_1$-$C_6$ alkylthio, nitro, halo, carboxy, and amido.

* * * * *

UNITED STATES PATENT AND TRADEMARK OFFICE
CERTIFICATE OF CORRECTION

PATENT NO. : 5,250,676

DATED : October 5, 1993

INVENTOR(S) : Catherine M. Gasparski, et al

It is certified that error appears in the above-indentified patent and that said Letters Patent is hereby corrected as shown below:

Column 17, lines 1-10, should be

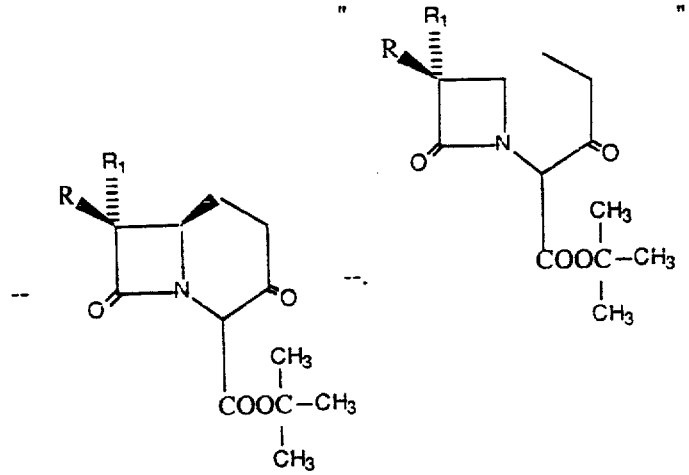

Signed and Sealed this

Fourth Day of October, 1994

*Attest:*

BRUCE LEHMAN

*Attesting Officer*   Commissioner of Patents and Trademarks